(12) United States Patent
Irwin

(10) Patent No.: US 12,178,930 B2
(45) Date of Patent: Dec. 31, 2024

(54) ROOM SANITIZATION SYSTEM

(71) Applicant: Stephanie Irwin, Moody, AL (US)

(72) Inventor: Stephanie Irwin, Moody, AL (US)

( * ) Notice: Subject to any disclaimer, the term of this patent is extended or adjusted under 35 U.S.C. 154(b) by 801 days.

(21) Appl. No.: 17/345,529

(22) Filed: Jun. 11, 2021

(65) Prior Publication Data

US 2021/0386892 A1 Dec. 16, 2021

Related U.S. Application Data

(60) Provisional application No. 63/039,147, filed on Jun. 15, 2020.

(51) Int. Cl.
*A61L 2/22* (2006.01)
*A61L 2/24* (2006.01)

(52) U.S. Cl.
CPC ............ *A61L 2/22* (2013.01); *A61L 2/24* (2013.01); *A61L 2202/14* (2013.01); *A61L 2202/15* (2013.01); *A61L 2202/25* (2013.01)

(58) Field of Classification Search
CPC .......... A61L 2/22; A61L 2/24; A61L 2202/14; A61L 2202/15; A61L 2202/25; A61L 2/18; A61L 2/183; A61L 2/186
See application file for complete search history.

(56) References Cited

U.S. PATENT DOCUMENTS

| 4,479,611 A | * | 10/1984 | Galvis | B05B 15/74 239/205 |
| 9,463,343 B2 | * | 10/2016 | Koiwa | A62C 37/12 |
| 2015/0258233 A1 | * | 9/2015 | Brown | A61L 2/24 422/292 |
| 2020/0222934 A1 | * | 7/2020 | Krutskevych | A62C 37/09 |

* cited by examiner

*Primary Examiner* — Timothy C Cleveland
(74) *Attorney, Agent, or Firm* — Brennan, Mann & Diamond, LLC

(57) ABSTRACT

The present invention relates to a room sanitization system that allows all surfaces in a room to be sanitized with a sanitizing and/or disinfecting solution. The room sanitization system is comprised of a plurality of sprinkler heads that may be controlled by a main hub that supplies each sprinkler head with the sanitizing disinfectant that is sprayed out of each head in a radial fashion. In addition, the main hub controls the frequency, intensity and duration of each sprinkler head during the disinfection process. Alternatively, the operation of the system may be controlled remotely via an electronic device. Each sprinkler head retracts within the surface in which it is installed, therefore remaining out of sight when not in use.

18 Claims, 4 Drawing Sheets

ROOM SANITIZATION SYSTEM

CROSS-REFERENCE TO RELATED APPLICATION

The present application claims priority to, and the benefit of, U.S. Provisional Application No. 63/039,147, which was filed on Jun. 15, 2020 and is incorporated herein by reference in its entirety.

FIELD OF THE INVENTION

The present invention relates generally to the field of sanitization. More specifically, the present invention relates to a room sanitization system that allows all surfaces within the room or other enclosed space to be properly sanitized via an aerosol disinfectant. The system is comprised of a reservoir or tank of a sanitizing or disinfecting solution, a plurality of sprinkler heads and related piping that are in fluid communication with the reservoir, and a main hub that controls the operation of each of the sprinkler heads and supplies the same with the disinfecting or sanitizing solution from the reservoir such that the solution is sprayed out of each head in a generally radial fashion. In addition, the main hub controls the frequency, intensity and duration of each sprinkler head throughout the disinfection process. Further, each sprinkler head is repositionable such that it retracts into the surface in which it is installed, thereby remaining out of sight when not in use. Accordingly, the present disclosure makes specific reference thereto. Nonetheless, it is to be appreciated that aspects of the present invention are also equally applicable to other like applications, devices and methods of manufacture.

BACKGROUND OF THE INVENTION

Humans come into contact with approximately sixty-thousand different types of germs on a daily basis. Said germs are present on a variety of surfaces, such as locations in homes, schools, hospitals, businesses, and many other structures. Although individuals may attempt to clean all surfaces within a room or structure to eliminate germs on said surfaces, it is not feasible to do so using traditional sanitizing means.

Attempting to manually clean all surfaces within a room or structure is extremely time-consuming, especially if done by only one individual. As such, the cleaning of all surfaces could take hours depending upon the size of the room and the efficiency of the individual doing the cleaning. Further, there is no guarantee that the individual doing the cleaning has adequality sanitized all surfaces, or even sanitized every surface at all.

To attempt to aid in the manual cleaning of surfaces, aerosol disinfectant sprays are sometimes used in order to more easily clean surfaces. However, these sprays are normally housed in a spray bottle or can, which still must be manually actuated to spray the disinfectant onto the surfaces that need disinfecting. In lieu of ineffective disinfectant sprays, foggers or atomizers may be used in order to spread disinfectant spray throughout a room more effectively. However, said devices are extremely unsightly and unnecessarily large, and cannot be easily hidden when not in use.

Therefore, there exists a long-felt need in the art for a room sanitization system that allows for the effective sanitization of all surfaces within a room or structure. Further, there exists a long-felt need in the art for a room sanitization system that results in the effective sanitization of all surfaces within the room or structure in a timely manner and without the need for substantial amounts of manual labor or involvement. Additionally, there exists a long-felt need in the art for a room sanitization system that is repositionable so as to not be unsightly or readily visible when not in use. Moreover, there exists a long-felt need in the art for a room sanitization system that may be remotely operated by a user using an electronic device and a wireless communication channel. Finally, there exists a long-felt need in the art for a room sanitization system that is relatively inexpensive to manufacture, and that is both safe and easy to use.

The subject matter disclosed and claimed herein, in one embodiment thereof, comprises a repositionable room sanitization system. The system is preferably housed within the ceiling of a room, wherein a plurality of repositionable and rotatable sprinkler heads extend downwardly from the ceiling to spray a sanitizing solution throughout the room. The sanitization process can further be automated to commence at certain times through the day via a main hub control, and may also be controlled remotely via a mobile software application on a smart device. The hub may also comprise a container-like device that houses disinfectant spray/aerosol that is supplied to the system via a plurality of tubing or piping. In addition, the hub may further comprise an air compressor, propellant or other forced-air system that propels the disinfectant through the tubing and out of each sprinkler head.

In this manner, the room sanitization system of the present invention accomplishes all of the forgoing objectives and provides an efficient and automated process to adequately sanitize all surfaces within a room. Further, the system requires no manual input other than the initial programming of the main hub. In addition, the system retracts into the ceiling and/or walls when not in use, and therefore is not unsightly.

SUMMARY

The following presents a simplified summary in order to provide a basic understanding of some aspects of the disclosed innovation. This summary is not an extensive overview, and it is not intended to identify key/critical elements or to delineate the scope thereof. Its sole purpose is to present some general concepts in a simplified form as a prelude to the more detailed description that is presented later.

The subject matter disclosed and claimed herein, in one embodiment thereof, comprises a room sanitization system. The system is comprised of a plurality of sprinkler heads that can be installed in the ceiling and/or walls of a room, enclosed space or other structure. When not in use, the sprinkler heads remained recessed in the ceiling and/or walls and therefore out of sight. However, when in use, the sprinkler heads may drop down from the ceiling or extend outwardly from a wall, and be used to spray a disinfecting and/or sanitizing spray/aerosol in a rotating fashion around the room or other enclosed space. In addition, the rotation of the heads may further be powered by a forced-air pressure system.

The programming and usage of the sanitizing system is further controlled via a main hub that may be installed within the room, or within a central area within a building or structure. The main hub allows a user to program the time and frequency that the system is operational, as well as the intensity of the system. In addition, the main hub may be further comprised of a replaceable aerosol cartridge that supplies aerosol/disinfectant to the system, and an air compressor that propels the disinfectant through a plurality of tubing or piping to each sprinkler head.

In a further embodiment of the present invention, the room sanitization system may further comprise a battery for powering the various components of the system, as well as a wireless communication module. The wireless communication module may be paired or otherwise in communication with a mobile application on an electronic device, such as a smartphone, smartwatch, remote control, computer, etc. In this manner, the room sanitation system of the present invention can be operated remotely by a user that is not present within the room, or even within the building containing the room.

In yet another embodiment of the present invention, the room sanitation system may further comprise one or more sensors (e.g., motion sensors, etc.) in wireless communication with the hub and/or the wireless communication module, and that prevent operation of the sanitization system if, for example, motion is detected within the room to be sanitized. In this manner, individuals are not unnecessarily exposed to the sanitizing/disinfecting solution as it is being expelled through the plurality of sprinkler heads.

Therefore, the room sanitization system of the present invention is particularly advantageous as it allows for a room to be easily and thoroughly sanitized without the need for manual cleaning. Further, the system allows for said sanitization to take place on a regularly and automatically scheduled basis, or to be remotely controlled. Finally, the room sanitization system can be repositioned out of sight when not in use, therefore rendering it more desirable than other portable or stationary sanitization devices.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION

Figure 1:
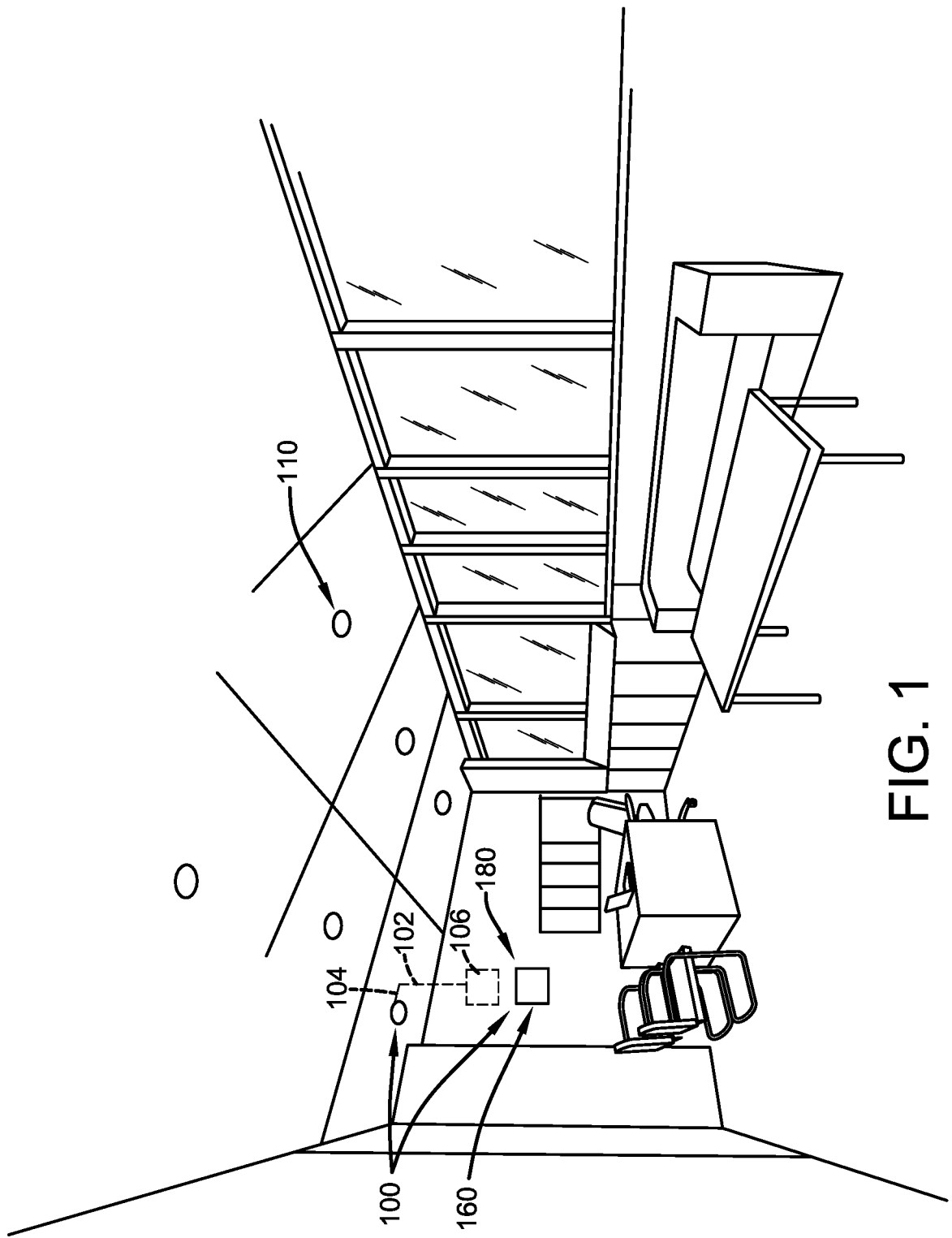
FIG. 1 illustrates a perspective view of one potential embodiment of a room sanitization system of the present invention installed within a room and within a ceiling in a retracted position in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention and do not limit the scope of the invention. Additionally, an illustrated embodiment need not have all the aspects or advantages shown. Thus, in other embodiments, any of the features described herein from different embodiments may be combined.

As noted above, there is a long-felt need in the art for a room sanitization system that allows for the effective sanitization of all surfaces within a room or structure. Further, there exists a long-felt need in the art for a room sanitization system that results in the effective sanitization of all surfaces within the room or structure in a timely manner and without the need for substantial amounts of manual labor or involvement. Additionally, there exists a long-felt need in the art for a room sanitization system that is repositionable so as to not be unsightly or readily visible when not in use. Moreover, there exists a long-felt need in the art for a room sanitization system that may be remotely operated by a user via an electronic device and a wireless communication channel. Finally, there exists a long-felt need in the art for a room sanitization system that is relatively inexpensive to manufacture, and that is both safe and easy to use.

The present invention, in one exemplary embodiment, is a room sanitization system comprised of a plurality of sprinkler heads that are preferably installed within a ceiling and/or walls of a room, enclosed space or structure. Each sprinkler head is in fluid communication with a main control hub and a reservoir or container of sanitizing and/or disinfecting solution via a series of piping and/or tubing. The main control hub controls the operation of the sanitization system and may comprise a battery or other electrical supply, one or more user controls, a wireless communication module, one or more sensors, and a pump, compressor or other propellant for discharging the sanitizing and/or disinfecting solution though each of the plurality of sprinkler heads. When the system is operational, each sprinkler head descends from the ceiling and/or extends outwardly from the wall and rotates, thereby spreading the disinfecting/sanitizing spray throughout the room or other space to adequately sanitize all surfaces within the same. The user controls and/or wireless communication module of the main hub also allow a user to easily program the frequency, duration, and intensity of the sanitization system and the operation of the plurality of sprinkler heads.

Referring initially to the drawings, FIG. 1 illustrates a perspective view of one potential embodiment of a room sanitizing system 100 of the present invention installed within a room and within a ceiling 10 in a retracted position in accordance with the disclosed architecture. The system 100 is primarily comprised of a plurality of sprinkler heads 110 and a main hub 160 for controlling and fueling the system 100. Nonetheless, in an alternative embodiment, the system may further comprise a reservoir 102 containing a sanitizing solution 106 that is separate and apart from the main hub 160 and that is in fluid communication with each of the plurality of sprinkler heads 110 via a series of pipes 104, tubes 1620 or other conduit. It should be noted that although the system 100 is preferably installed within a ceiling 10, the system 100 may be installed within any surface of a room or structure such as the walls of the room/structure, the floor of the room/structure, the roof of the room/structure or any combination thereof. It is further contemplated that when in a retracted position (e.g. not in use), the system 100 sits flush with whatever surface it is installed within.

Figure 2A:
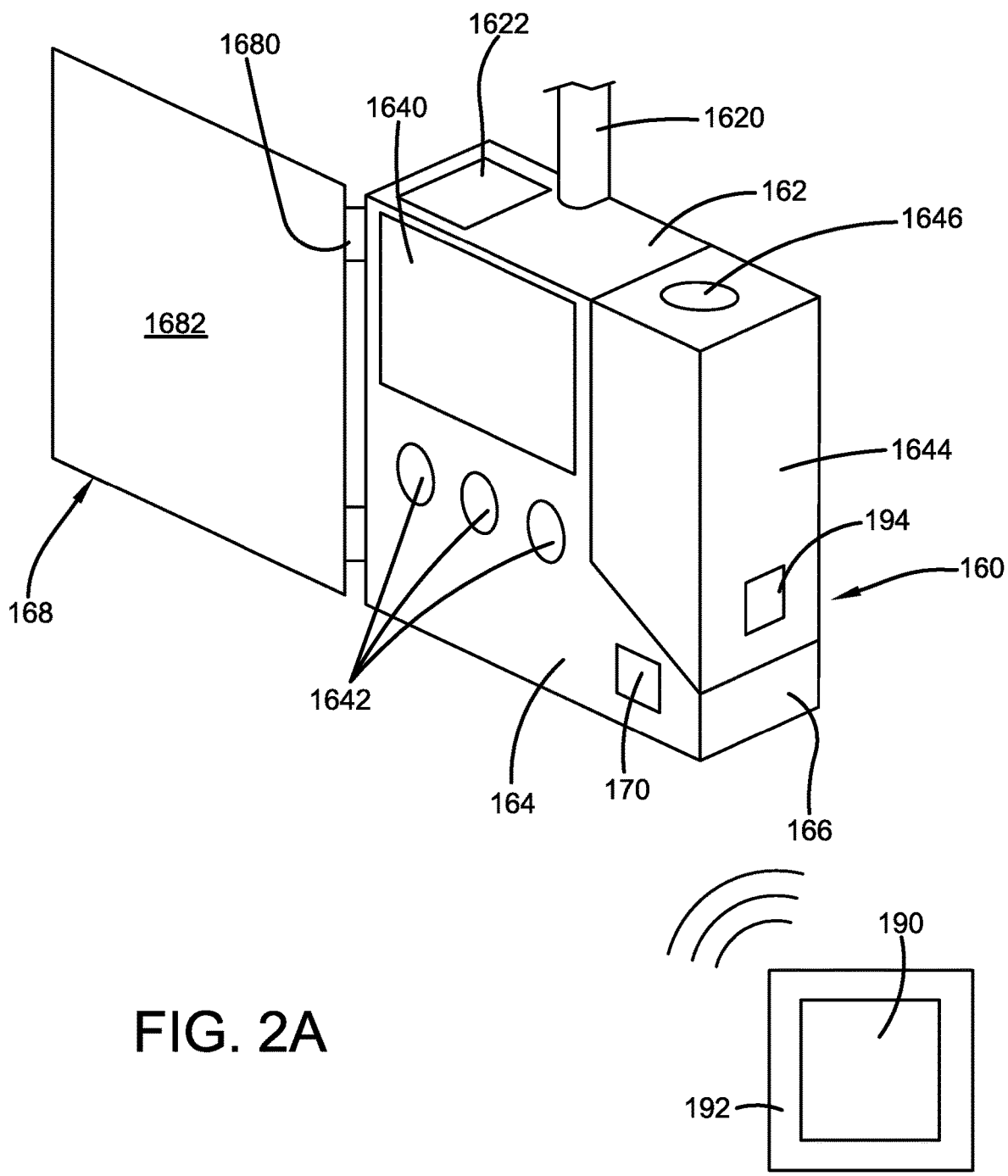
FIG. 2A illustrates a perspective view of one potential embodiment of a main hub of the room sanitization system of the present invention with the cover in an open position in accordance with the disclosed architecture.
Figure 2B:
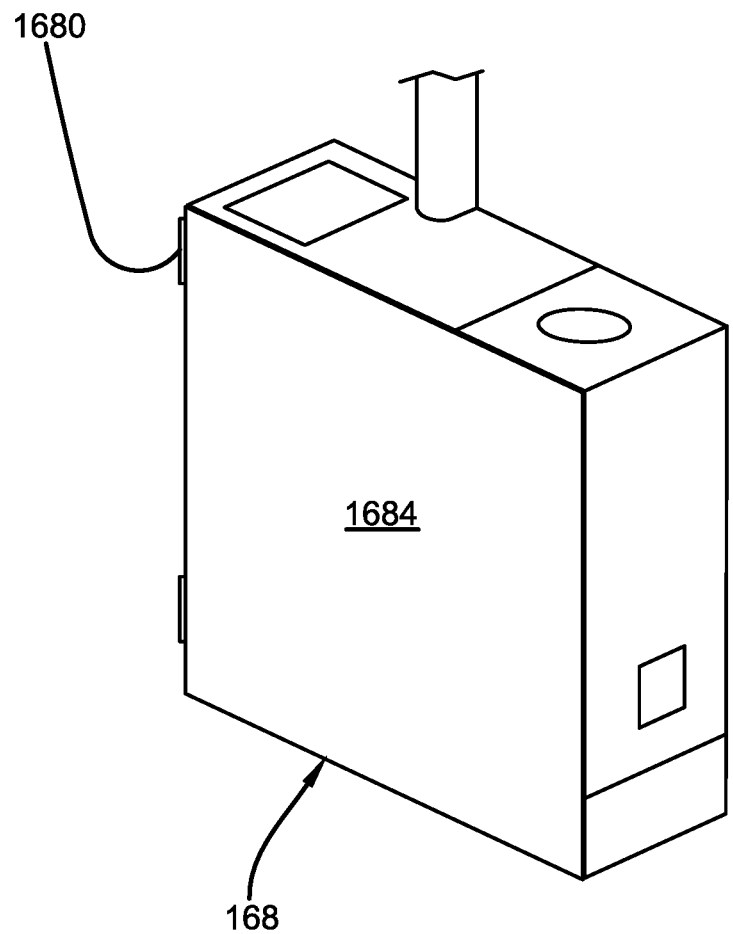
FIG. 2B illustrates a perspective view of one potential embodiment of a main hub of the room sanitization system of the present invention with the cover in a closed position in accordance with the disclosed architecture.

FIG. 2A illustrates a perspective view of one potential embodiment of a main hub 160 of the room sanitizing system 100 of the present invention with a cover 168 in an open position in accordance with the disclosed architecture. The main hub 160 serves as the control center of the system 100, wherein each sprinkler 110 or all sprinklers 110 can be programmed to run independently or synchronously with one another via the hub 160. The programming of the system can be accomplished via a series of control buttons 1642 on the side surface 164 of the generally square hub 160, or via a touch-screen display 1640 that also is located on a side surface 164. It is further contemplated that in differing embodiments, each button 1642 may have a unique function, such as, but not limited to: power (on/off), intensity of spraying, duration, frequency, etc. Accordingly, the system 100 can be programmed to run automatically at various times throughout the day based on factors such as the time of day or frequency (ex. every thirty minutes, every hour, etc.). As such, in on embodiment of the system 100 wherein the system 100 spans multiple rooms within a structure, the main hub 160 may allow a user to program the system 100 such that different portions of the system 100 located in different areas or rooms of the structure will be activated or deactivated during certain time periods or in accordance with certain frequencies and/or intensities.

In the shown embodiment of the hub 160, the hub 160 is generally square in shape and is comprised of a top surface 162, two sets of generally parallel side surfaces 164, and a bottom surface 166. However, in differing embodiments of the system 100 the hub 160 may be a plurality of shapes such as but not limited to: spherical, oblong, rectangular, triangular, etc. Further, the hub 160 may be installed on, or within (e.g. such that it is flush) with the surface of a wall, as shown in FIG. 1, by conventional fastening means and fasteners such as screws, bolts, adhesive, etc.

One side surface 164 of the hub 160 is also comprised of a removable aerosol container 1644. This container 1644, which may be in the form of a can, bottle, reservoir, etc., houses all the liquid aerosol disinfectant that is supplied to the system 100 via tubing 1620 that connects to each sprinkler 110 such that the disinfectant can be sprayed by each sprinkler 110. In differing embodiments, the container 1644 may be refillable (e.g. reusable) via a threaded cap 1646 or may be a single-use disposable that can be replaced when it runs out of liquid aerosol disinfectant. The hub 160 may also be comprised of an air compressor 1622 or forced-air system that allows forced air to enter into the tubing 1620 to propel disinfectant to each sprinkler 110, and to power each sprinkler 110 will be explained more fully below.

As noted, the hub 160 may also be comprised of a cover 168 that is attached to the hub 160 via at least one hinge 1680, as shown in FIG. 2A wherein the cover 168 is in an opened position (e.g. not covering the hub 160). It is further contemplated that the inner surface 1682 of the cover 168 shields the buttons 1642, touch screen 1640 and container 1644 from view when in a closed position, especially in an embodiment of the system wherein the hub 160 is embedded into a wall. Further, the outer surface 1684 of the cover 168 may be comprised of a veneer or façade that matches the texture or material of the ceiling 10 or surface the hub 160 is installed within. As such, this cover 168 further allows the hub 160 to be concealed and blend in with a wall, ceiling, or other surface it is embedded in or attached to, especially when the hub 160 is installed flush with a wall or ceiling 10 surface.

Figure 3:
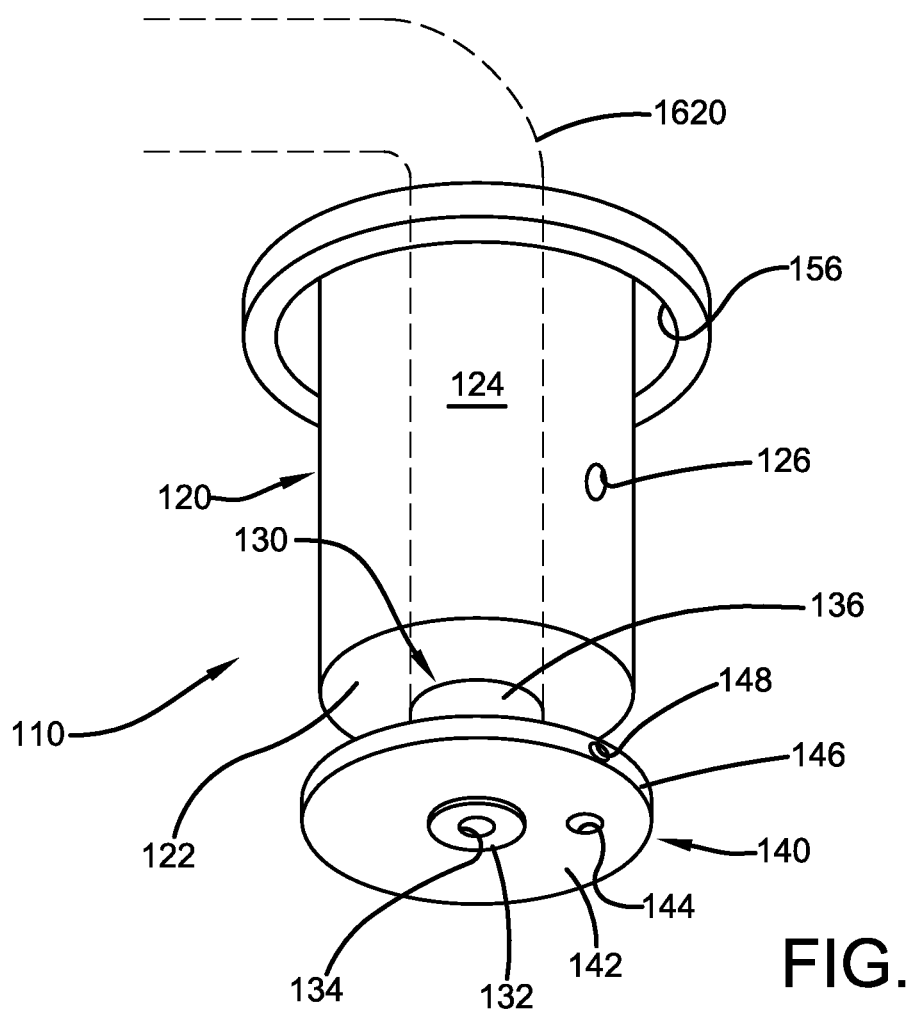
FIG. 3 illustrates a perspective view of one potential embodiment of a repositionable sprinkler assembly of the room sanitization system of the present invention in a deployed position in accordance with the disclosed architecture.

FIG. 3 illustrates a perspective view of one potential embodiment of a sprinkler assembly 110 of a room-sanitizing system 100 of the present invention in a deployed position in accordance with the disclosed architecture. In differing embodiments of the system 100, the number of sprinklers 110 that are included in the system 100 may vary, based on the size of the room or structure the system 100 is installed within. Each sprinkler 110 is comprised of a body 120, a shaft 130 and a head 140. The body 120 is preferably cylindrical in shape and is comprised of a flat top surface 122 and a continuous side surface 124. The shaft 130 further runs through the body 120 wherein it is fixedly or separably attached to the tubing 1620 to receive disinfectant. Like the body 120, the shaft 130 is generally cylindrical and is comprised of a flat top surface 132 and a continuous side surface 136. The top surface 132 of the shaft 130 is further fixedly connected to the head 140. The head 140 is then comprised of a generally flat, circular top surface 142 as well as a side surface 146. It is contemplated that in the preferred embodiment of the head 140, it is comprised of a veneer or façade that matches the texture or material of the ceiling 10 or surface the system 100 is installed within.

Further, it is preferred that the top surface 132 of the shaft 130 protrudes through the center of the head 140. It is also contemplated that the top surface 132 of the shaft is comprised of at least one continuous opening 134 that allows disinfectant to exit the shaft 130 while the head 140 and/or shaft 130 rotates to disperse disinfectant in all directions. However, in one embodiment of the sprinkler 110, the body 120 may also rotate simultaneously or independent of the shaft 130 and/or head 140. Further, the side surface 124 of the body 120 may be comprised of at least one continuous opening 126 that allows disinfectant to exit the body 120. This is also true for the top surface 142 and side surface 146 of the head 140, which can also be comprised of at least one continuous opening 144, 148 to allow disinfectant to exit the head 140.

It is further contemplated the deployment, retraction, and rotation of each sprinkler 110 may be powered by the compressor 1622 of the system 100 in the form of forced air. However, in differing embodiments, the deployment, retraction, and rotation of each sprinkler 110 may be powered by an electric motor 115 within each sprinkler unit, wherein each motor 115 may be in electrical communication and receive power from the main hub 160 via electrical wiring.

Figure 4:
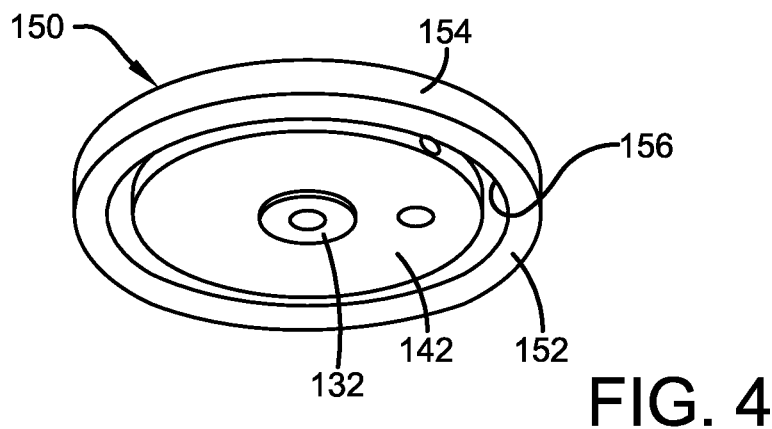
FIG. 4 illustrates a perspective view of one potential embodiment of a sprinkler assembly of a room sanitizing system of the present invention in a retracted position in accordance with the disclosed architecture.

FIG. 4 illustrates a perspective view of one potential embodiment of a sprinkler assembly 110 of a room sanitizing system 100 of the present invention in a retracted position in accordance with the disclosed architecture. Each sprinkler 110 sits within a continuous opening 156 within a housing 150 that is preferably fixedly embedded within a ceiling 10 surface or other surface that each sprinkler 110 may be installed in. The housing 150 is comprised of a reinforced top surface 152 and side surface 154, which may extend slightly beyond the surface of the ceiling 10 or may be completely flush with the surface of the ceiling 10. In any embodiment, the top surface 152 and side surface 154 may be comprised of a veneer or façade that matches the texture or material of the ceiling 10 or surface the system 100 is installed within.

Additionally, in one exemplary embodiment of the present invention, the room sanitization system 100 may further comprise an RFID tag or other wireless communication module 170 embedded in, for example, the main hub 160 or positioned along its various components that may be wirelessly paired with a mobile application 190 on a remote electronic device 192, as best shown in FIG. 2A. The wireless communication module 170 may be powered by a battery 194 or hardwired into the existing electrical system of the room or other space, and the remote electronic device 192 may be, but is not limited to, a smartphone, smart watch, computer, tablet or the like. The wireless communication module 170 may also be in communication with an electrically-wired structure within the plurality of sprinkler heads 110, or through wireless connectivity, to extend or retract the sprinkler heads 110, as desired, via the mobile application 190/electronic device 192.

In yet another embodiment of the present invention, the room sanitation system 100 may further comprise one or more sensors 180 (e.g., motion sensors, etc.), as best shown in FIG. 1. The sensors 180 are preferably in wireless communication with the hub 160 and/or the wireless communication module 170, and can be used to prevent operation of the sanitization system 100 if, for example, motion is detected within the room to be sanitized. In this manner, individuals are not unnecessarily exposed to the sanitizing/disinfecting solution 106 as it is being expelled through the plurality of sprinkler heads 110.

Certain terms are used throughout the following description and claims to refer to particular features or components. As one skilled in the art will appreciate, different persons may refer to the same feature or component by different names. This document does not intend to distinguish between components or features that differ in name but not structure or function. As used herein "sanitization system", "disinfection system", and "system", are interchangeable and refer to the room sanitization system 100 of the present invention.

Notwithstanding the forgoing, the room sanitization system 100 of the present invention and its various components can be of any suitable size and configuration as is known in the art without affecting the overall concept of the invention, provided that they accomplish the above-stated objectives. One of ordinary skill in the art will appreciate that the size, configuration and material of the room sanitization system 100 as shown in the FIGS. are for illustrative purposes only, and that many other sizes and shapes of the room sanitization system 100 are well within the scope of the present disclosure. Although the dimensions of the room sanitization system 100 are important design parameters for user convenience, the room sanitization system 100 may be of any size, shape and/or configuration that ensures optimal performance during use and/or that suits the user's needs and/or preferences.

Various modifications and additions can be made to the exemplary embodiments discussed without departing from the scope of the present invention. While the embodiments described above refer to particular features of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A room sanitization system comprising:
   a main hub;
   a plurality of sprinkler heads; and
   a supply of sanitizing or disinfecting solution in fluid communication with each of the plurality of sprinkler heads; and
   wherein deployment, retraction, and rotation of each sprinkler head is powered by a compressor; and
   wherein each sprinkler head comprises a concealing veneer surface.

2. The room sanitization system of claim 1 further comprising a power source, a set of user controls, and a length of piping connecting the supply of sanitizing or disinfecting solution with each of the plurality of sprinkler heads.

3. The room sanitization system of claim 2 further comprising at least one sensor, a wireless communication module, and a remote electronic device in communication with the wireless communication module.

4. The room sanitization system of claim 1, wherein each of the plurality of sprinkler heads is retracted into a ceiling or a wall when in a stowed position.

5. The room sanitization system of claim 1, wherein each of the plurality of sprinkler heads extend outwardly from a ceiling or a wall when in a deployed position.

6. A room sanitization system comprising:
   a main hub comprised of a control panel, a power supply, a propellant and a container;
   a plurality of sprinkler heads;
   a network of pipes forming a watertight connection between the container and each of the plurality of sprinkler heads; and
   a supply of sanitizing or disinfecting solution stored in the container; and
   wherein the control panel comprises a touch-screen display comprising a spray intensity control button, a spray duration button, and a spray frequency button; and
   wherein the main hub further comprises a hinged cover configured to shield the touch-screen display, the hinged cover comprising an outer surface comprising a concealing veneer surface; and
   wherein deployment, retraction, and rotation of each sprinkler head is powered by a sprinkler motor.

7. The room sanitization system of claim 6 further comprising at least one sensor positioned in a room, a wireless communication module, and a software application installed on a remote electronic device that is in communication with the wireless communication module, wherein the at least one sensor will prevent operation of the room sanitization system if a motion is detected in the room.

8. The room sanitization system of claim 7, wherein a user can use the remote electronic device to remotely control the room sanitization system.

9. The room sanitization system of claim 8, wherein each of the plurality of sprinkler heads is both rotatable and repositionable between a deployed position and a stowed position.

10. The room sanitization system of claim 9, wherein each of the plurality of sprinkler heads are retracted into a ceiling or a wall in the room when in the stowed position.

11. The room sanitization system of claim 9, wherein each of the plurality of sprinkler heads extend outwardly from a ceiling or a wall in the room when in the deployed position.

12. A room sanitization system comprising:
a plurality of sprinkler heads each comprised of a body, a shaft, and a head that are housed in a recessed housing in a wall, a floor or a ceiling;
a main hub; and
an aerosol container containing an aerosol disinfectant and an integrated air compressor, wherein the aerosol container is in communication with each of the plurality of sprinkler heads; and
a touch-screen display comprising a spray intensity control button, a spray duration button, and a spray frequency button; and
wherein each sprinkler head further comprises a concealing veneer surface; and
wherein deployment, retraction, and rotation of each sprinkler head is powered by the integrated air compressor.

13. The room sanitization system of claim 12 further comprising at least one sensor and a wireless communication module.

14. The room sanitization system of claim 13, wherein the at least one sensor is a motion sensor.

15. The room sanitization system of claim 14 further comprising a remote electronic device with a software application installed thereon that is in communication with the wireless communication module.

16. The room sanitization system of claim 15, wherein each of the plurality of sprinkler heads is both rotatable and repositionable between a deployed position and a stowed position.

17. The room sanitization system of claim 16, wherein each of the plurality of sprinkler heads is retracted into the recessed housing when in the stowed position.

18. The room sanitization system of claim 16, wherein each of the plurality of sprinkler heads extend outwardly from the ceiling, the floor or the wall when in the deployed position.

* * * * *